(12) United States Patent
Tooren et al.

(10) Patent No.: US 11,633,517 B2
(45) Date of Patent: Apr. 25, 2023

(54) BIOMEDICAL POLYURETHANES

(71) Applicant: Polyganics IP B.V., Groningen (NL)

(72) Inventors: Martin Franke Tooren, Bedum (NL); Dirk Erik Muller, Assen (NL); Konstantin Igorovitch Denisov, Leeuwarden (NL)

(73) Assignee: Polyganics IP B.V., Groningen (NL)

( * ) Notice: Subject to any disclaimer, the term of this patent is extended or adjusted under 35 U.S.C. 154(b) by 288 days.

(21) Appl. No.: 16/089,582

(22) PCT Filed: Mar. 31, 2017

(86) PCT No.: PCT/NL2017/050201
§ 371 (c)(1),
(2) Date: Sep. 28, 2018

(87) PCT Pub. No.: WO2017/171550
PCT Pub. Date: Oct. 5, 2017

(65) Prior Publication Data
US 2019/0099518 A1   Apr. 4, 2019

(30) Foreign Application Priority Data

Mar. 31, 2016   (NL) ..................... 2016526

(51) Int. Cl.
  *A61L 27/18*   (2006.01)
  *A61L 27/50*   (2006.01)
  (Continued)

(52) U.S. Cl.
  CPC ............. *A61L 27/18* (2013.01); *A61L 27/507* (2013.01); *A61L 27/58* (2013.01); *A61L 27/60* (2013.01);
  (Continued)

(58) Field of Classification Search
None
See application file for complete search history.

(56) References Cited

U.S. PATENT DOCUMENTS 6,087,465 A * 7/2000 Seppala ............. C08G 18/4283
                                                        525/450
6,784,273 B1 * 8/2004 Spaans .................... A61L 27/18
                                                        528/65
(Continued)

FOREIGN PATENT DOCUMENTS

| CN | 102002142 A * | 4/2011 | |
| EP | 2842583 A1 * | 3/2015 | ......... C08G 18/6674 |
| WO | 99/64491 A1 | 12/1999 | |
| WO | 2004/074342 A1 | 9/2004 | |

OTHER PUBLICATIONS

Rokicki et al., "ROP of Cyclic Carbonoates and ROP of Macrocycles," Polymer Science: A Comprehensive Reference, pp. 247-287, (2012) (Year: 2012).*

(Continued)

*Primary Examiner* — Randy P Gulakowski
*Assistant Examiner* — Ha S Nguyen
(74) *Attorney, Agent, or Firm* — Banner & Witcoff, Ltd.

(57) ABSTRACT

The invention is directed to biomedical polyurethanes. The invention is particularly directed to biomedical polyurethanes with improved biodegradability and to an improved preparation of the biomedical polyurethanes. In particular the present invention provides a biomedical polyurethane having the formula $(A-B-C-B)_n$, wherein A denotes a polyol, B denotes a diisocyanate moiety, C denotes a diol component and n denotes the number of recurring units, and wherein the B-C-B segment is bioresorbable.

10 Claims, 5 Drawing Sheets

Figure 1:
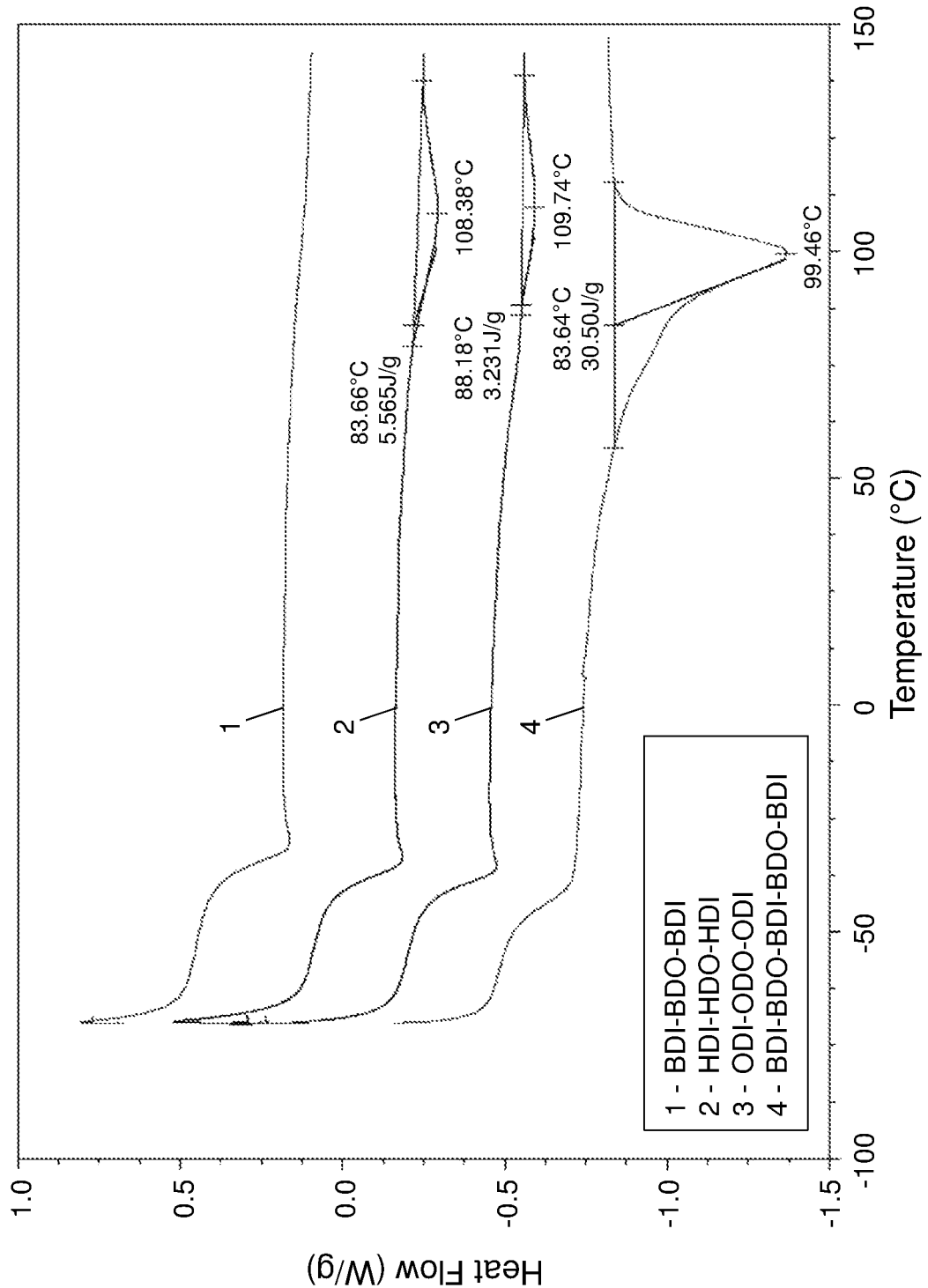

(51) Int. Cl.
*A61L 27/58* (2006.01)
*A61L 27/60* (2006.01)
*C08G 18/73* (2006.01)
*C08G 18/42* (2006.01)
*C08G 18/44* (2006.01)
*C08G 18/75* (2006.01)
*C08G 18/77* (2006.01)
*C08G 18/24* (2006.01)
*C08J 9/28* (2006.01)
*C08L 75/06* (2006.01)
*C08G 18/10* (2006.01)
*C08G 18/32* (2006.01)

(52) U.S. Cl.
CPC ............ *C08G 18/42* (2013.01); *C08G 18/73* (2013.01); *A61L 2430/06* (2013.01); *A61L 2430/32* (2013.01)

(56) References Cited

U.S. PATENT DOCUMENTS

2007/0015894 A1* 1/2007 Heijkants .............. C08G 18/10
　　　　　　　　　　　　　　　　　　　528/44
2009/0093565 A1　4/2009 Yang et al.
2009/0099600 A1* 4/2009 Moore ................ C08G 18/664
　　　　　　　　　　　　　　　　　　　606/246

OTHER PUBLICATIONS

Stridsberg, "Controlled Ring-Opening Polymerization: Polymers with designed Macromolecular Architecture," Department of Polymer Technology Royal Institute of Technology Stockholm, Sweden, pp. 1-84, 2000 (Year: 2000).*

* cited by examiner

BIOMEDICAL POLYURETHANES

RELATED APPLICATIONS

This application is a National Stage Application under 35 U.S.C. 371 of co-pending PCT application PCT/NL2017/050201 designating the United States and filed Mar. 31, 2017; which claims the benefit of NL application number 2016526 and filed Mar. 31, 2016 each of which are hereby incorporated by reference in their entireties.

The invention is directed to biomedical polyurethanes. The invention is particularly directed to biomedical polyurethanes with improved biodegradability and to an improved preparation of the biomedical polyurethanes.

Biomedical polyurethanes (PUs) have been used for a wide range of applications. Examples include nerve guides, meniscal reconstruction materials, artificial skin and artificial veins.

WO99/64491, which is incorporated herein in its entirety, describes biomedical polyurethanes based on diisocyanate linked polyester polymer and diol components, said diol component having a uniform block-length.

The PUs of WO99/64491 have a number of drawbacks. It has been found that the biodegradability of the biomedical polyurethane is limited and some mass (about 20 wt %) of a typical polyurethane remains even after prolonged exposure of the polyurethane to biodegrading conditions at elevated temperatures (see e.g. J. Zuidema et al., *Journal of Biomedical Materials Research Part A* (2008) p. 920-930).

It is desirable to provide biomedical polyurethanes with improved solubility and biodegradability characteristics, while maintaining the favorable mechanical properties, such as high resistance to tearing for which the polyurethanes of WO99/64491 are known.

The present inventors have found that this may be achieved by biomedical polyurethanes having the general formula $(A-B-C-B)_n$, wherein A denoted a polyol, B denotes a diisocyanate moiety, C denotes a diol component and n denotes the number of recurring units, and wherein B-C-B' is bioresorbable.

For the sake of clarity and conciseness the composition of the polymers and the segments described herein may be defined by and named after the building blocks or monomers from which the polymers and polymer segments are made, or on which they are based. However, if the polymer or polymers segments can be obtained by using different building blocks or monomers, whilst resulting in the same composition (structure), such polymer or polymers segments are included by the specific definition or name as is used herein as well.

Without wishing to be bound by theory, the present inventors believe that the poor biodegradability of conventional polyurethanes as described in the prior art, may be attributed to the limited solubility of hard 5-block segments with a uniform length on which these conventional polyurethanes are based (e.g. BDI-BDO-BDI-BDO-BDI, wherein BDI denotes 1,4-butane diisocyanate and BDO denotes 1,4-butane diol). The present inventors found that the improved biodegradability of the biomedical PU is achieved by improving the solubility of the urethane (B-C-B) segment, which in turn may be achieved by decreasing the crystallinity of the urethane segment.

If has been found that a urethane segment wherein at least one, preferably both of the diisocyanate moieties (B) in B-C-B is of a different length than the diol component (C) results in a urethane segment that is bioresorbable.

With the lengths of the diisocyanate moiety and the diol component is meant the length of the parts of the moiety or component that is present in the backbone of the polyurethane. The length of the diisocyanate moiety (B) can also be expressed as the length between the two isocyanate groups of a diisocyanate compound on which the urethane segment is based. Similarly, the length of the diol component (C) can also be expressed as the length between the two hydroxyl groups of a diol compound on which the urethane segment is based. A practical way to express the length of the diisocyanate moiety and the diol component is by the number of atoms of each moiety and/or component present in the backbone of the urethane segment between the urethane moiety. For instance, a urethane segment based on 1,6-hexane diisocyanate (HDI) and 1,4-butane diol (i.e. B-C-B being HDI-BDO-HDI) thus comprises two diisocyanate moieties having a length of six atoms and a diol component having a length four atoms.

In contrast to polyurethanes comprising a urethane segment with diisocyanate moieties and a diol component having the same length, the hard segment wherein the diisocyanate moiety (B) is of a different length than the diol component (C) has a decreased crystallinity; likely since the urethane moieties in the urethane segments are less well aligned for hydrogen bonding. The limited hydrogen bonding is believed to result in a reduced crystallinity.

It is described in WO99/64491 that the uniformity of the urethane-based urethane segments is the crucial factor for the mechanical properties of the materials. However, the present inventors have surprisingly found that similar mechanical properties can also be obtained by having urethane segments with a multiform length and that this multiformity in fact improves the biodegradability of the biomedical polyurethane.

In a particular embodiment of the present invention, the B-C-B segment (also referred to herein as urethane segment) of the biomedical polyurethane has a multiform block length.

The terms "segment" and "block" as used herein, refer to a polymeric structure of any length. In the art of polymer technology, a long polymeric structure is often referred to as a block, whereas a short polymeric structure is often referred to as a segment. Both these conventional meanings are understood to be comprised in the term "segment" as well as in the term "block" as used herein.

It may be appreciated that, as is common in the field of polymer chemistry, the polyurethane of the present invention may in fact have a certain polymeric weight distribution. When referring herein to the biomedical polyurethane, also a mixture of polyurethanes based on different compounds is meant. This mixture may be the result of different types of polyol (soft) segment and/or of different types of the urethane segment. For instance, the urethane segment may be based on a mixture of different diols (C) and/or diisocyanates (B). Similarly, a single polyurethane polymer molecule may comprise a mixture of B-C-B segments. In fact, the polyurethanes comprising a urethane segment with a multiform block length are typically obtained by having a mixture of different diols (vide infra). Moreover, the diisocyanates B in the polyurethane according to formula (A-B-C-B) may be the same or may be different. Accordingly, a certain single B-C-B segment within the polyurethane may comprise two of the same or two different diisocyanates B. In fact, polyurethanes that are made according to a method of the present invention wherein a mixture of diisocyanates are used (vide infra), are typically having different diisocyanates B in a single B-C-B segment. Similarly, the polyurethane may also comprise a mixture of different polyols or a single type of polyol.

In contrast to polyurethanes comprising a urethane segment with a uniform length, the multiform block lengths result in a system wherein the urethane segment has decreased crystallinity, since the urethane moieties in the urethane segments are not well aligned for hydrogen bonding. The limited hydrogen bonding is believed to result in a reduced crystallinity.

The reduced crystallinity, and as such the improved biodegradability, can already be observed by having only a small amount (e.g. 5 mol %) of urethane segments with a diverging length. Preferably, less than 95 mol %, more preferably less than 80 mol %, even more preferably less than 70 mol %, most preferably less than 60 mol % of the B-C-B segments are having the same length.

A particular facile way to express the block length of the urethane segment is by the (theoretical) number of linear atoms comprised in the backbone of the segment excluding the three atoms comprised in each urethane bond (i.e. —O—C(O)—NH—), which can be e.g. determined upon the preparation of the polyurethane (vide infra). Preferably, the urethane segments comprise on average of more than 12, preferably more than 14, more preferably more than 16 linear atoms in the back bone.

The mechanical properties of the materials (e.g. a sheet) based on the polyurethane of the present invention preferably have a modulus of 1-50 MPa. A 3.5 wt % foam prepared by solvent casting (vide infra) has typical a compression of between 2.5 and 10 kPa.

The inventors have further surprisingly found that the biodegradability of the urethane segment can also be increased by limiting the number of urethane bonds per (A-B-C-B) unit, which are capable of forming the hydrogen bonds, to four or less. As such, it is preferred that the B-C-B is based on two diisocyanate units. Again, without wishing to be bound by theory, limiting the hydrogen bonding is believed to result in a reduced crystallinity. Since B denotes a diisocyanate block, it is thus preferred that C is not based on a diisocyanate block. As a result, such polyurethane does not comprise a 5-block urethane segment but instead comprises a 3-block urethane segment.

It was found that for the embodiment wherein B-C—B is based on two diisocyanate units and is of a uniform block length, the biodegradability of the B-C-B segment is generally better than uniform blocks having being based on more than two (e.g. three) diisocyanate units (e.g. B-C-B-C-B blocks). As such, in this particular embodiment, the B-C-B segment may be of a uniform block length, however this is not always required and the B-C-B segment may also be of a multiform length and/or a segment wherein the diisocyanate moiety (B) is of a different length than the diol component (C) as described herein above.

As explained herein above, it has been found that the length of the urethane segment influences the mechanical properties of the polyurethane. It has been found that in case the polyurethane comprising a urethane segment that is based on two diisocyanate units, good mechanical properties are obtained if the B-C-B segment comprises more than 12, preferably more than 14, more preferably more than 16 linear carbon atoms in the back bone.

In a preferred embodiment, the B-C-B segment of the present invention is non-crystalline. The bioresorbability and/or crystallinity of the B-C-B segment can be assessed using various methods.

It has been found that in case the thermal properties of the polyurethane of the present invention is determined by thermal analysis such as differential scanning calorimetry (DSC), the urethane segment does not have a melting peak. This is in strong contrast to the (hard, uniform, and crystallizing) urethane segments in polyurethanes as described in WO99/64491. In a preferred embodiment of the present invention, the B-C-B segment thus essentially does not have a melting peak as determined by DSC.

An alternative method to assess the bioresorbability of the B-C-B segment is by carrying out an in vitro degradation study, wherein a sample of the polyurethane is exposed to degradation medium, typically Sörensen buffer solution with a pH of 7.4 and kept in an incubator at 37° C. according to ISO 10993. At certain intervals, the remaining mass of the sample is analyses. In a preferred embodiment of the present invention, less than 10 wt. % of the polyurethane remains after 16 h of exposure to a buffer solution with a pH of 7.4 at 37° C.

In preferred embodiments of the present invention, B is at least partially based on a linear or branched $C_4$ to $C_{11}$ alkyl diisocyanate, preferably selected from the group consisting of 1,4-butane diisocyanate (BDI), 1,5-pentane diisocyanate (PDI), 1,6-hexyl diisocyanate (HDI), 1,7-heptyl diisocyanate (HpDI), 1,8-octyl diisocyanate (ODI), 1,9-nonyl diisocyanate (NDI), 1,10-decyl diisocyanate (DDI), methylene bis(4-cyclohexylisocyanate), 2,6-diisocyanatohexanoate and esters thereof (L-lysine diisocyanate, LDI), 5-isocyanate-1-(isocyanomethyl)-1,3,3-trimethylcyclohexane (isophorondiisocyanate, IPDI), and combinations thereof.

In preferred embodiments of the present invention, C is at least partially based on linear or branched $C_4$ to $C_{11}$ alkyl diol, preferably selected from the group consisting of glycol, diethylene glycol, 1,4-butane diol (BDO), 1,5-pentane diol (PDO), 1,6-hexyl diol (HDO), 1,7-heptyl diol (HpDO), 1,8-octyl diol (ODO), 1,9-nonyl diol (NDO), 1,10-decyl diol (DDO), N-methyl diethanolamine (N-MDEA), 2,2-bis(hydroxymethyl)propanoic acid, tartaric acid, polyethylene glycol, polycaprolactone, poly lactide and combinations thereof.

In the embodiment wherein the urethane segment is of a multiform length, C may also be a diol that is a XYX reaction product of diol (X) and diisocyanate (Y), wherein diol (X) is a diol selected from the group consisting of glycol, diethylene glycol, 1,4-butane diol (BDO), 1,5-pentane diol (PDO), 1,6-hexyl diol (HDO), 1,7-heptyl diol (HpDO), 1,8-octyl diol (ODO), 1,9-nonyl diol (NDO), 1,10-decyl diol (DDO), N-methyl diethanolamine (N-MDEA), 2,2-bis(hydroxymethyl)propanoic acid, tartaric acid, polyethylene glycol, polycaprolactone, poly lactide and combinations thereof and diisocyanate (Y) is a diisocyanate selected from the group consisting of 1,4-butane diisocyanate (BDI), 1,5-pentane diisocyanate (PDI), 1,6-hexyl diisocyanate (HDI), 1,7-heptyl diisocyanate (HpDI), 1,8-octyl diisocyanate (ODI), 1,9-nonyl diisocyanate (NDI), 1,10-decyl diisocyanate (DDI), methylene bis(4-cyclohexylisocyanate), 2,6-diisocyanatohexanoate and esters thereof (L-lysine diisocyanate, LDI), 5-isocyanate-1-(isocyanomethyl)-1,3,3-trimethylcyclohexane (isophorondiisocyanate, IPDI) and combinations thereof.

The mechanical properties of the polyurethane can be further improved by allowing C to comprise a small amount (e.g. 0.01 to 10 mol %) of triol. Examples of suitable triols include glycerol, triethanolamine, and the like. The presence of a small amount of triol may result in a (partial) cross-linking of the polyurethane.

At least part of the diol C may be substituted with a $C_1$-$C_{10}$ hydrocarbon, comprising a carboxylic acid, nitrile, isonitrile or protected S, N, P or O, for instance with a propionic acid side group. These groups enable further functionalization of the polyurethane with for instance an activated ester, an acid chloride, an anhydride, an aldehyde, p-nitrophenyl carbonate, an epoxide, an isocyanate, a vinyl sulfone, maleimide, o-pyridyl-disulfide or a thiol. Examples of substituted diols that are suitable are 5-hydroxy-3-(hydroxymethyl)valeric acid, 2,2-bis(hydroxymethyl)propanoic acid, tartaric acid, and the like.

With the number of linear atoms in the back bone of a block is meant the smallest number of atoms that are located in the back bone of a block. For instance, when the backbone comprises a cyclic moiety such as IPDI, the smallest number of atoms between the urethane bonds (i.e. are to be counted. Thus, e.g. in the case of a IPDI-ODO-IPDI block, the number of linear atoms in the backbone of the block is 16 (4+8+4).

The polyol can comprise any diol, triol, tetraol, etc. or a mixture thereof. For instance, the polyol can comprise any of the diols described herein for the diol component C in $-(A-B-C-B-)_n$. Polyol A may comprise the same or different diol molecules as diol component C does. In preferred embodiments, the polyol has an average molecular weight in the range of 500 to 10000 g/mol.

Preferably, the polyol comprises a prepolymer. Examples of suitable prepolymers include poly(alkene oxides) such as polyethylene glycol (PEG), polyesters such a polycaprolactone (PCL) or poly(lactic acid) (PLA), or mixtures thereof. Preferably, the prepolymer comprises a polyester.

Prepolymer that may be used in accordance with the present invention are disclosed in WO99/64491. The prepolymer to be used in accordance with the invention will preferably be linear, in particular it will comprise a polyester such as a random copolyester, and comprise reactive end groups. These end groups may be hydroxyl or carboxyl. It is preferred to have a dihydroxy terminated prepolymer, but hydroxy-carboxyl or dicarboxyl terminated prepolymer can also be used. The nature of the endgroups is determined by the type of co-monomers, the amounts thereof, the type of starter (if used), and the reaction conditions of the preparation of the prepolymer.

Suitable monomers for the prepolymer comprising the polyester are the cyclic monomers that can be polymerized under ring-opening polymerization conditions. Examples of cyclic monomers are lactide (L, D, LD, meso), glycolide, ε-caprolactone, δ-valerolactone, trimethylenecarbonate, tetramethylenecarbonate, 1,5-dioxepane-2-one, para-dioxanone, and combinations thereof. In a further preferred embodiment, A is a polyester derived from exclusively lactide and ε-caprolactone, typically with a molecular weight between 1000 and 4000.

In case the prepolymer is at least partially linear, it can be prepared using at least partially a difunctional component (e.g. a diol) as starter, but in case a tri- or higher than three functional components is used, star shaped prepolymers may be obtained.

In a particular embodiment of the present invention, the polyol segment comprises a hydrophilic segment. Examples of prepolymer segments comprising hydrophilic segments are described in WO2004/062704, which is incorporated herein in its entirety. The presence of the hydrophilic segment increases the absorption capacities of the device based on the polyurethane polymer and may also influence the rate of biodegradation. The hydrophilic segment may for instance be derived from polypeptide, poly(vinyl alcohol), poly(vinylpyrrolidone), poly(hydroxymethylmethacrylate) or polyethers. A hydrophilic segment is preferably a polyether, such as poly(ethylene glycol).

In case the polyol segment comprises a hydrophilic segment, said polyol segment preferably comprises polyethylene glycol in a content of 1-80 wt %, more preferably 5-60 wt %, even more preferably 20-50 wt %, most preferably 50 wt %.

In a most preferred embodiment, the polyol segment is a prepolymer segment based on about 25 wt. % lactide, about 25 wt. % ε-caprolactone and about 50 wt. % of polyethylene glycol.

The products of the present invention show a good balance between the properties necessary for use thereof in biomedical applications, such as good modulus, tensile strength and compression modulus. It has been found possible to process these materials into porous implants by salt-leaching and freeze-drying, typically resulting in a material having macropores in the range of 150 μm to 300 μm. The material can also be produced in situ in an extruder, even in combination with generating macropores in situ.

A further aspect of the present invention is the preparation of biomedical polyurethanes.

Conventional methods, including the method described in WO99/64491, are based on reacting a prepolymer (e.g. a dihydroxy-terminated polyester) with a large excess of a diisocyanate. A drawback of this method is that the excess of diisocyanate needs to be removed, generally by distillation, before the polyol can be chain extended with the diol. This makes the method cumbersome and inflexible, in particular since not all diisocyanates are removable by distillation. For the preparation of the present biomedical polyurethanes, it is preferred to have a method for preparation in which larger (and heavier) diisocyanates (e.g. diisocyanates comprising 8 or more carbon atoms) can be used to obtain B-C-B segments that are based on only two diisocyanate units while the B-C-B segment has the desired minimal length (e.g. at least 12 carbon atoms), and which method allows for a more precise control of the ratio of different types of building blocks of B and/or C.

It was found that the method of the present invention requires only half the time compared to the conventional method as described in WO99/64491.

In accordance with the invention, there is provided a method for the preparation of the biomedical polyurethane having the formula $(A-B-C-B)_n$, wherein A denoted a polyol, B denotes a diisocyanate moiety, C denotes a diol component and n denoted the number of recurring units has been developed, said method comprising the step of i) reacting the polyol A with diisocyanate B to form an isocyanate terminated polyol B-A-B, followed by;

ii) determining the amount of isocyanate groups [R—NCO], followed by;

iii) reacting the isocyanate terminated polyol B-A-B with the diol component C to form the biomedical polyurethane having the formula $(A-B-C-B)_n$.

Advantageously, the method of the present invention biomedical polyurethane enable precise control over the ratio of the A and B-C—B and/or the length of the polymer by selecting to appropriate relative ratios of A, B and C.

In a particular embodiment, in step i), about 1 equivalent of diisocyanate B (compared to the amount of reactive end-groups of the polyol A) is reacted. For instance, in case the polyol is linear and comprises only two reactive end groups (e.g. the polyol is a diol), the resulting polymers are of the formula $(A-B-C-B)_n$.

However, the relative amount of diisocyanate B in step i) may be in the range of 1 to 1.5 equivalents, preferably in the range of 1 to 1.2 equivalents (compared to the amount of reactive end-groups of the polyol A). For instance, in case the ratio is 1.5 and the polyol is linear and comprises only two reactive end groups (e.g. the polyol is a diol), the resulting polymers are of the formula (B-A-B-C-B-C)$_n$. Ratio between 1:1.5 and 1:1 typically lead to mixtures of polymers having formulae (A-B-C-B)$_n$ and (B-A-B-C-B-C)$_n$ The precise molecular weight and thus the precise number of reactive end groups of the polyol is in practice unknown. As such, the number of reactive end groups may only be estimated and the amount of diisocyanate B that needs to be added in order to add 1 equivalents thereof, is also an estimation. As such, about 1 equivalents of diisocyanate B (compared to the amount of reactive endgroups of the polyol) are added.

In a particular embodiment of the present invention, the prepolymer may be prepared by reacting an initiator compound (e.g. a diol such as polyethylene glycol (PEG)) with monomers (e.g. one or more lactones such as caprolactone, lactide, glycolide, trimethylene carbonate and/or caprolacton). The initiator may be a diol (PEG, BDO, DEG, HDO, ODO, etc) or multiarmed alcohols (pentaerythritol, hexaglycerol, sorbitol). By varying the amount of initiator compared to the monomers, the length and molecular weight of the prepolymer can be influenced.

The mechanical properties of the polyurethane may be influenced by the weight ratio of polyol versus urethane segment. The desired weight ratio can be obtained by providing a polyol with an appropriate molecular weight. With a shorter polyol, the polyurethane comprises relatively more of the urethane segment which is believed to result in an increase of hydrogen bridges in the polyurethane and concomitantly different mechanical properties compares to a polyurethane comprising less urethane segments. Typically, the weight ratio polyol A to (B-C-B) is in the range of 1:1 to 25:1, preferably in the range of 2:1 to 15:1, for instance about 5:1.

For instance, good mechanical properties can be obtained in case a polyol having an average molecular weight of 2000 g/mol is used, in combination with BDI-ODO-BDI as B-C-B segment (having a molecular weight of 426.51 g/mol), a polyurethane is obtained having a weight ratio polyol A to (B-C-B) of about 5:1 (100 to 21.326).

Although in theory, precisely 2 equivalent of the diisocyanate moieties will react with the polyol if the polyol is a diol, in practice this is typically not the case, for instance because the precise molecular weight and precise number of reactive end groups of the polyol are not known. As such, to determine the amount of reacted diisocyanate moieties, the amount of isocyanate groups [R—NCO] is determined in step ii). Based on this amount, an equimolar amount of the diol component C is used to form the biomedical polyurethane. The amount of isocyanate groups [R—NCO] can be determined by known techniques such as titration or Fourier transform infra-red spectroscopy (FT-IR).

An advantage of the present invention is that any diisocyanate may be used in step i), thus also diisocyanates that can not be removed by distillation. Moreover, a mixture of diisocyanates can be used. This mixture may be reacted with the polyol at once, or first a first diisocyanate may be reacted followed by the reaction of a second diisocyanate. By using a mixture of diisocyanates, a polyurethane with a multiform B-C-B block length may be obtained.

In yet another embodiment, two or more different isocyanate terminated polyols may be prepared, which are subsequently mixed and used in step ii) and iii).

In a preferred embodiment of the present invention, the amount of the isocyanate groups [R—NCO] is monitored during step iii). As such, it is known when the reaction has reached full conversion. The amount of the isocyanate groups [R—NCO] is preferably monitored by FT-IR.

In a particular embodiment, an equimolar amount of diols (compared to the amount of isocyanate groups [R—NCO]) is reacted in step iii). Alternately, a sub-equimolar amount of diols (compared to the amount of isocyanate groups [R—NCO], e.g. 50 mol %) is reacted, after which the remaining (unreacted) isocyanate groups [R—NCO]) can be reacted with water (typically under elevated temperatures). For instance, in case less than 1 equivalent of diol C is added, shorter polymers of the formula (A-B-C-B)$_n$ are formed when compared to 1 equivalent of diol C. Preferably, the amount of C is not more than 1 equivalent since this can result in hydroxyl-terminated polymers, which is undesired.

In another preferred embodiment, a mixture of diols is used as the diol component C. For instance, the diol component C may comprise two or more different diol compounds that differ in their respective lengths. The mixture of diols may be reacted with the isocyanate terminated polyol B-A-B at once, or first a first diol may be reacted followed by the reaction of a second diol. By using a mixture of diisocyanates, a polyurethane with a multiform B-C-B block length may be obtained. In the embodiment wherein first a first diol is reacted, it is particularly preferred to monitor the amount of the isocyanate groups [R—NCO] during step iii).

It is generally preferred that the diol component C is not based on a diisocyanate block. As a result, such the prepared polyurethane does not comprise a 5-block urethane segment but instead comprises a 3-block urethane segment. It is found that when the diol component C does comprise a diisocyanate block, polyurethanes comprising 7- and even 9-block urethane segments are formed during step iii).

The method of the present invention further comprise a step of forming a medical device such as a foam or a sheet of the biomedical polyurethane. This step may comprise for instance solvent casting and freeze drying.

A particular further aspect of the present invention is a polyurethane obtainable by the method as described herein above.

For the purpose of clarity and a concise description features are described herein as part of the same or separate embodiments, however, it will be appreciated that the scope of the invention may include embodiments having combinations of all or some of the features described.

The invention can be illustrated with the following examples.

EXAMPLE 1

A polyol (50 g, 0.025 mol, 2000 g/mol) was synthesized from DL-lactide and ∈-caprolactone using PEG1000 (i.e. PEG having an average. molecular weight of 1000 g/mol) as an initiator and stannous octoate as a catalyst at a temperature of 140° C. for 14-17 days under nitrogen atmosphere. The polyol was subsequently reacted with 3.5 g (0.05 mol, 2 eq.) of butanediisocyanate (BDI). After complete conversion (within 1 h), the concentration isocyanates ([NCO]) was determined using FT-IR. This [NCO] is used to determine the amount of chain extender diol component (1,6-hexanediol) which needs to be added to obtain the 3-block polyurethane. The following equation was used:

$$\text{Mass } HDO(\text{mg}) = \frac{[NCO] \times (m_{polymer} + m_{BDI}) \times M_{HDO}}{2} \times 0.98$$

1,4-dioxane was added as the solvent (ratio 1:1) and the reaction mixture was heated to 90° C. The reaction mixture became viscous over time and the [NCO] was monitored during the reaction using FT-IR. After complete conversion of the available NCO groups, the reaction mixture was diluted with 1,4-dioxane. The obtained polymer could be processed into foams by freeze-drying or into sheets/tubes using solvent casting.

EXAMPLE 2

A polyol (50 g, 0.025 mol, 2000 g/mol) was synthesized from DL-lactide and ∈-caprolactone using PEG1000 as an initiator and stannous octoate as a catalyst at a temperature of 140° C. for 14-17 days under nitrogen atmosphere. Gelpermeation chromatography (GPC) and ¹H-NMR showed complete conversion of the monomers. The polyol was subsequently reacted with 3.5 g (0.05 mol, 2 eq.) of butanediisocyanate (BDI). After complete conversion (within 1 h), the [NCO] was determined using FT-IR. This [NCO] was used to determine the amount of chain extender diol (1,8-octanediol) component which needs to be added to obtain the 3-block polyurethane. The following equation was used:

$$\text{Mass } HDO(\text{mg}) = \frac{[NCO] \times (m_{polymer} + m_{BDI}) \times M_{HDO}}{2} \times 0.98$$

1,4-dioxane was added as the solvent (ratio 1:1) and the reaction mixture was heated to 90° C. The reaction mixture became viscous over time and the [NCO] was monitored during the reaction using FT-IR. After complete conversion of the available NCO groups, the reaction mixture was diluted with 1,4-dioxane. The obtained polymer could be processed into foams by freeze-drying or into sheets/tubes using solvent casting.

EXAMPLE 3

A prepolymer (50 g, 0.025 mol, 2000 g/mol) was synthesized from DL-lactide and ∈-caprolactone using PEG1000 as an initiator and stannous octoate as a catalyst at a temperature of 140° C. for 14-17 days under nitrogen atmosphere. Gelpermeation chromatography (GPC) and ¹H-NMR showed complete conversion of the monomers. The prepolymer was subsequently reacted with 8.41 g (0.05 mol, 2 eq.) of hexanediisocyanate (HDI). After complete conversion (within 1 h), the [NCO] was determined using FT-IR. This [NCO] was used to determine the amount of chain extender diol component (BDO) which needs to be added to obtain the 3-block polyurethane. The following equation was used:

$$\text{Mass } HDO(\text{mg}) = \frac{[NCO] \times (m_{polymer} + m_{BDI}) \times M_{HDO}}{2} \times 0.98$$

1,4-dioxane was added as the solvent (ratio 1:1) and the reaction mixture was heated to 90° C. The reaction mixture became viscous over time and the [NCO] was monitored during the reaction using FT-IR. After complete conversion of the available NCO groups, the reaction mixture was diluted with 1,4-dioxane. The obtained polymer could be processed into foams by freeze-drying or into sheets/tubes using solvent casting.

EXAMPLE 4

A series of polyurethanes was prepared in a method similar to that of Examples 1-3. The same prepolymer was used, but different diisocyanate moieties and/or diol components were used.

Characterization

The properties of the prepared foams are provided in Tables 1 and 2. The intrinsic viscosity (IV) was measured using a falling ball microviscometer (Anton Paar) using a one-point measurement according to the Solomon-Ciuta approximation in chloroform as a solvent at 25° C. The thermal properties of the polymer where determined using a Q2000 (TA Instruments). The mechanical properties were determined using an Instron Tensile tester. The foam absorbance was determining the weight of a foam (3.5 wt % obtained by freeze-drying) with the weight of the same foam soaked in water (depicted as x times initial weight). The foam absorbance rate (mL/sec) was determined by measuring the weight of the foam after predetermined time intervals in a petri dish containing water.

Figure 2:
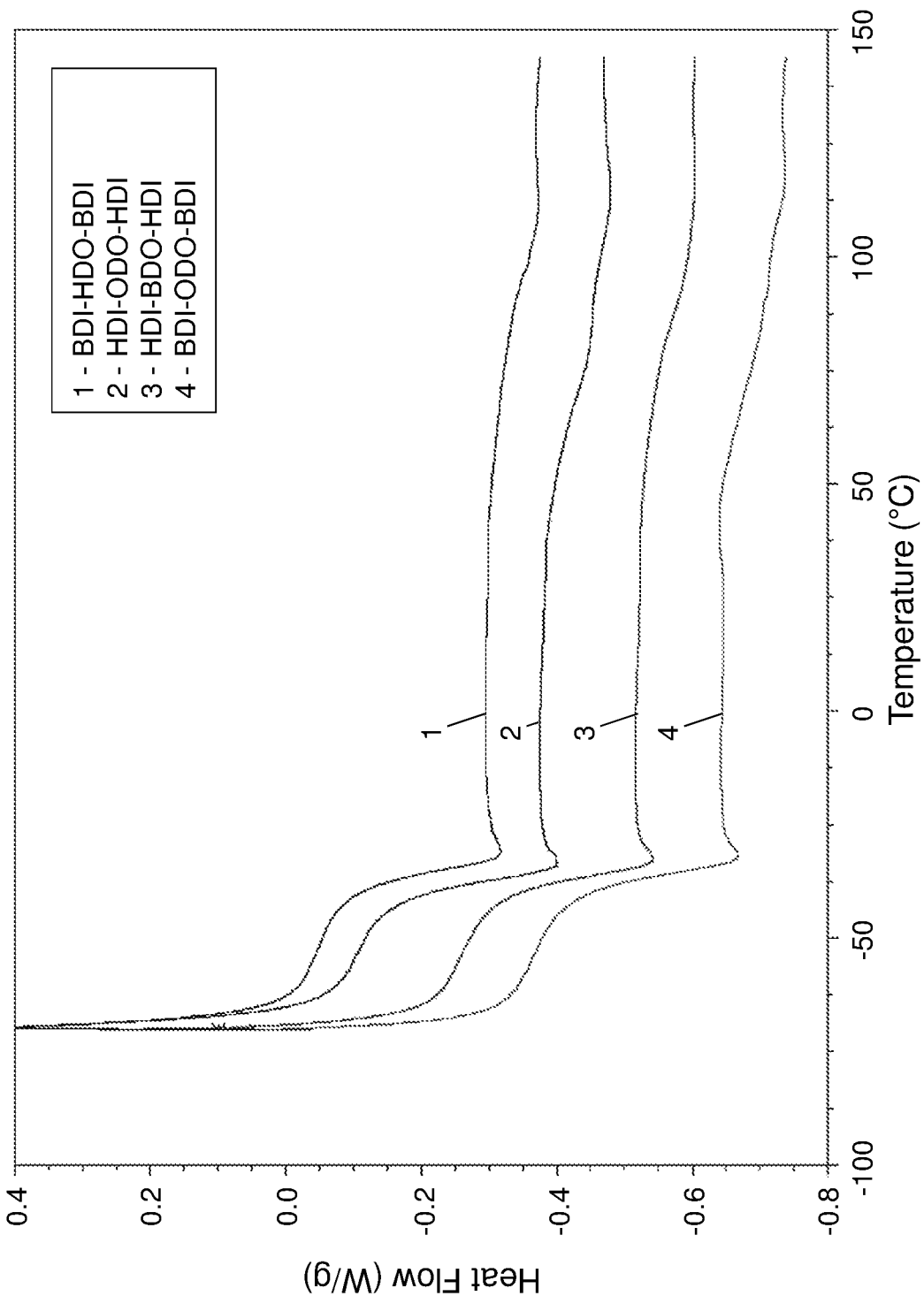

Calorimeter studies were carried out with the Q2000. The scanning rate was 10° C. per minute. The results are provided in FIGS. 1 and 2.

TABLE 1

| B-C-B | HDI-HDO-HDI | BDI-BDO-BDI-BDO-BDI | BDI-BDO-BDI |
|---|---|---|---|
| Tg (° C.) | −37.7 | −39.7 | −34.1 |
| Tm (° C.) | 108.3 | 96.0 | — |
| Foam absorbance (x initial weight) | 18.6 | 17.5 | — |
| Foam absorption rate (mL/sec) | 183 | 124 | — |
| Mw (g/mol) | 66200 | 56400 | — |
| Mn (g/mol) | 49900 | 35300 | — |
| IV (dL/g) | 1.0 | 1.8 | — |
| Modulus (MPa) | 12.5 | 37.4 | — |

TABLE 2

| B-C-B | HDI-ODO-HDI | HDI-BDO-HDI | BDI-ODO-BDI | BDI-HDO-BDI |
|---|---|---|---|---|
| Foam absorbance (x initial weight) | 19.2 | 17.6 | 19.4 | 17.2 |
| Foam absorption rate (mL/sec) | 267 | 199 | 286 | 254 |
| Mw (g/mol) | 61400 | 57700 | 63100 | 48800 |
| Mn (g/mol) | 44200 | 37400 | 41000 | 31300 |
| IV (dL/g) | 1.00 | 0.89 | 1.09 | 0.77 |
| Modulus (MPa) | 16.5 | 15.8 | 15.4 | 9.65 |

Method for In Vitro Degradation

The in vitro degradation studies of the prepared polyurethanes were performed in test tubes using Sorensen buffer solution with a pH of 7.4 as the degradation medium, kept in an incubator at 37° C. Sorensen buffer solution was prepared by mixing 18.2 wt % KH₂PO₄ (0.012 M) with 81.8 wt % NaH₂PO₄ (0.055 M). The buffer solutions were poured into 100 mL bottles. A polymer sample was added to each bottle and the sample was subsequently incubated for specific time periods. After time periods of 0, 0.5, 1, 3, 5, 7, 16, 44, 48, 72, 96, 168, 336, 672 and 2016 h, samples were removed from the bottles which were stored in the incubator, washed thoroughly with distilled water (5×10 mL) onto a 0.45 µm filter paper, frozen in a freezer overnight, freeze-dried for 24 h and the remaining sample was characterized with respect to thermal properties, weight, absorption, compression, IV and molecular weight distribution.

Figure 3:
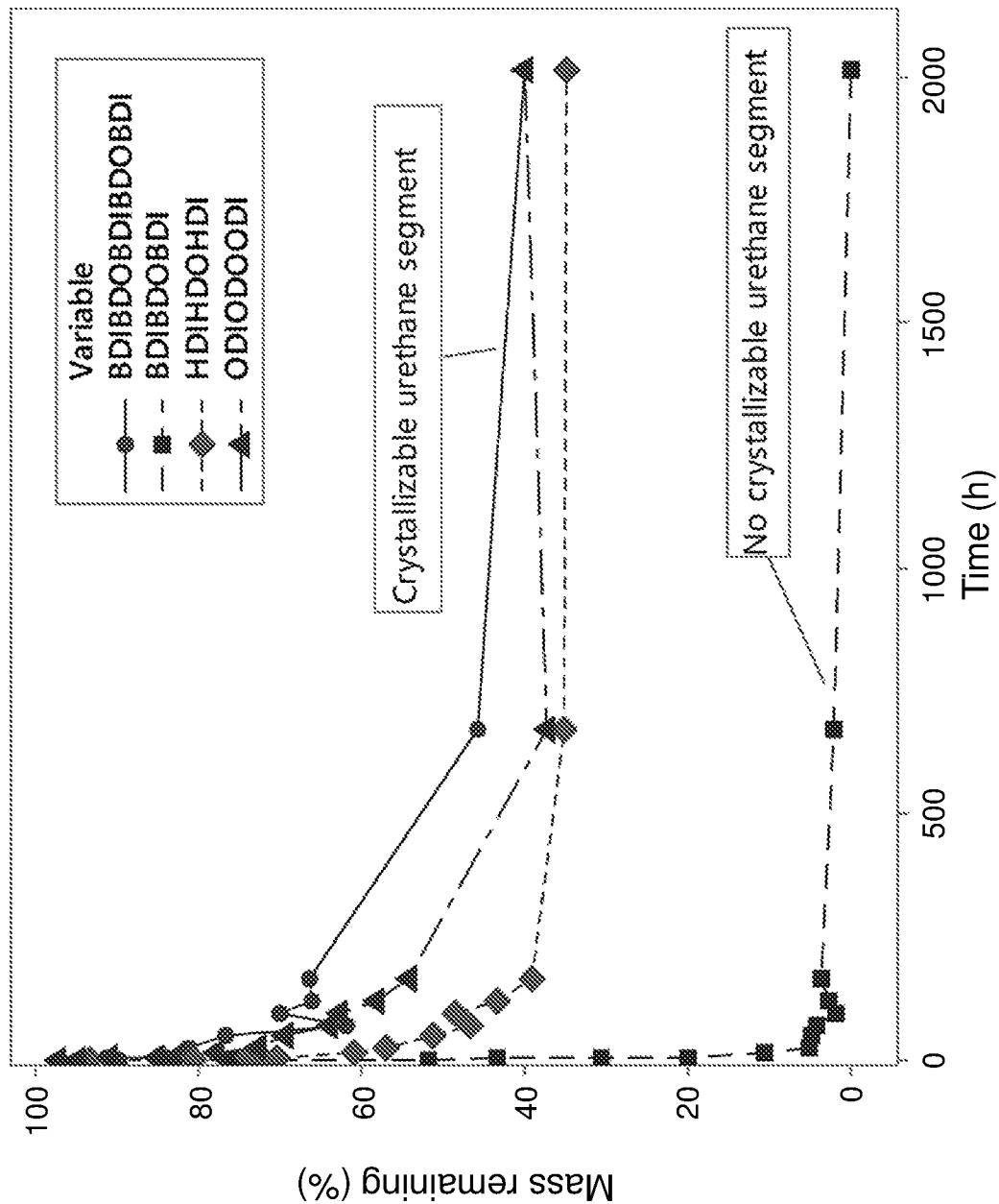
Figure 4:
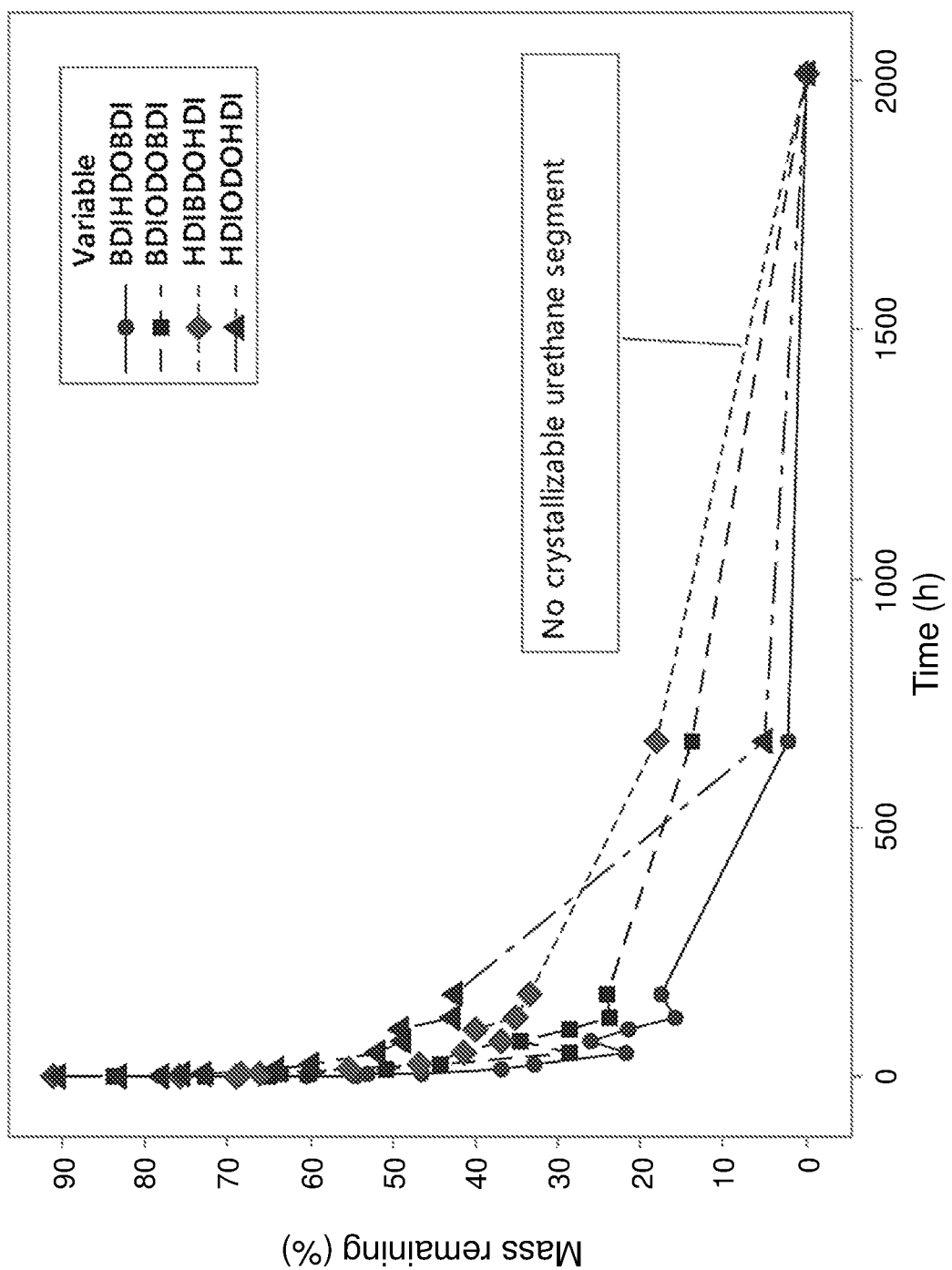

The results are provided in FIGS. 3 and 4.

EXAMPLE 5

A series of polyurethanes was prepared with a procedure similar to Example 2. The same prepolymer and diisocyanate (BDI) were used, but mixtures of diol components (BDO-BDI-BDO and N-MDEA in ratios of 50/50 to 100/0) were used to prepare polyurethanes comprising urethane segments having a pluriform length.

Figure 5:
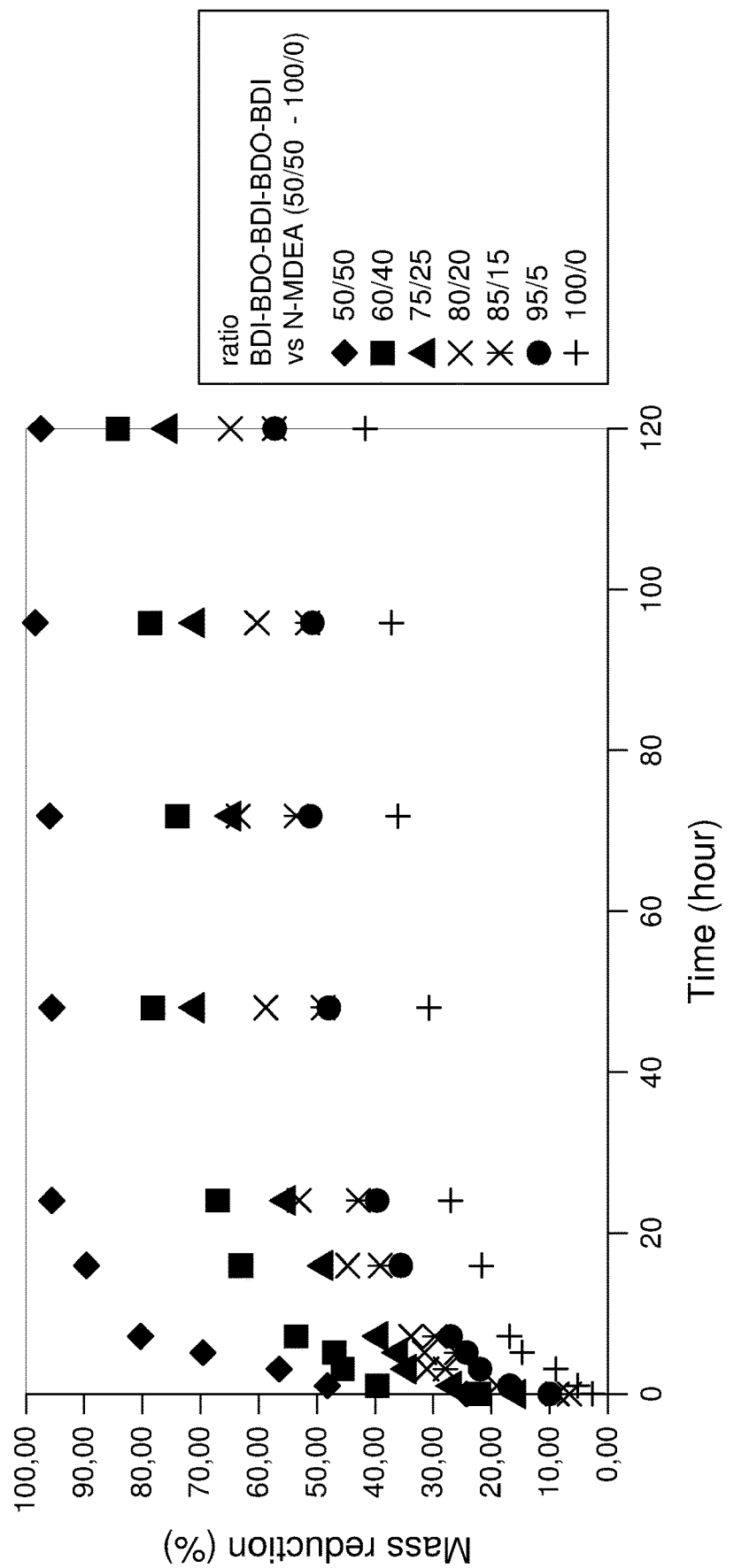

The biodegradability of the resulting polyurethanes was determined in a method for in vitro degradation as described in Example 4. The results are provided in FIG. 5.

The invention claimed is:

1. Biomedical polyurethane having the formula $-(A\text{-}B\text{-}C\text{-}B)_n$-, wherein A denotes a polyol comprising a prepolymer that is at least partially based on a random copolyester, wherein the polyol is a soft segment, B denotes 1,4-butane diisocyanate, C denotes 1,8-octanediol and n denotes the number of recurring units, wherein the B-C-B segment is bioresorbable.

2. Biomedical polyurethane according to claim 1, wherein the B-C-B segment has a multiform block length.

3. Biomedical polyurethane according to claim 1, wherein the copolyester is based on lactide, glycolide, trimethylene carbonate and/or ε-caprolactone.

4. Biomedical polyurethane according to claim 3, wherein the random copolyester is at least partially based on 5 to 95 mol % of lactide amd 5 to 95 mol % ε-caprolactone.

5. Biomedical polyurethane according to claim 1, for use in a method of the treatment of nasal wounds, nerves, meniscal injuries, skin and/or veins.

6. Medical device of a foam or a sheet, comprising the biomedical polyurethane according to claim 1.

7. Method for the preparation of a biomedical polyurethane in accordance with claim 1, said method comprising the step of:
  i) reacting the polyol A with the diisocyanate B to form an isocyanate terminated polyol B-A-B, followed by;
  ii) determining the amount of isocyanate groups [R—NCO], followed by;
  iii) reacting the isocyanate terminated polyol B-A-B with the diol component C to form the biomedical polyurethane having the formula $-(A\text{-}B\text{-}C\text{-}B)_n$-.

8. Method according to claim 7, wherein the amount of the isocyanate groups [R—NCO] is monitored during step iii).

9. Method according to claim 7, further comprising a step of forming a medical device such as a foam or a sheet of the biomedical polyurethane.

10. Method according to claim 7, wherein the amount of the isocyanate groups [R—NCO] is monitored during step iii) by using FT-IR.

* * * * *